United States Patent [19]

Koch et al.

[11] Patent Number: 5,739,535
[45] Date of Patent: Apr. 14, 1998

[54] OPTICAL GAS ANALYZER

[75] Inventors: Edmund Koch, Lübeck; Peter Dreyer, Pansdorf; Otto Rosinke, Lübeck; Gerd Peter, Lübeck; Wajih Al-Soufi, Lübeck, all of Germany

[73] Assignee: Drägerwerk Aktiengesellschaft, Lübeck, Germany

[21] Appl. No.: 731,204

[22] Filed: Oct. 10, 1996

[30] Foreign Application Priority Data

Oct. 25, 1995 [DE] Germany .......... 195 39 618.9
Jul. 13, 1996 [DE] Germany .......... 196 28 310.8

[51] Int. Cl.$^6$ .......... G01N 21/25; G01N 21/35
[52] U.S. Cl. .......... 250/339.13; 250/339.09; 250/351; 250/338.3; 356/437
[58] Field of Search .......... 250/339.13, 339.09, 250/343, 351, 338.3, 252.1 A, 252.1 R; 356/437

[56] References Cited

U.S. PATENT DOCUMENTS

| | | | |
|---|---|---|---|
| 4,692,621 | 9/1987 | Passaro et al. | 250/343 |
| 4,914,719 | 4/1990 | Conlon et al. | 250/339 |
| 5,013,920 | 5/1991 | Asano et al. | 250/343 |
| 5,070,245 | 12/1991 | Rantala et al. | 250/343 |
| 5,184,017 | 2/1993 | Tury et al. | 250/343 |
| 5,206,511 | 4/1993 | Apperson et al. | 250/343 |

FOREIGN PATENT DOCUMENTS

| | | |
|---|---|---|
| 0 087 077 A2 | 8/1983 | European Pat. Off. . |
| 0 332 180 A2 | 9/1989 | European Pat. Off. . |
| 0 307 625 B1 | 4/1994 | European Pat. Off. . |

OTHER PUBLICATIONS

Eltec Instruments, Inc., Feb. 1990, Introduction to Infrared Pyroelectric Detectors, Elec.

*Primary Examiner*—Edward J. Glick
*Assistant Examiner*—Darren M. Jiron
*Attorney, Agent, or Firm*—McGlew and Tuttle

[57] ABSTRACT

An optical gas analyzer for measuring the percentage of components in a gas phase by IR absorption, containing a power source, a measuring path containing the gas sample, a photoelectric receiver with an evaluation circuit arranged downstream of it, which receiver detects the IR radiation from the measuring path, and a plurality of filters, which can be introduced one after another into the beam path at a predetermined filter change frequency f, wherein measured signals belonging to the filters are sent by the receiver due to the radiation extinction in the measuring path, is to be improved such that different components in the gas sample can be detected in a simple manner and at good selectivity. To accomplish this object, the receiver is a pyroelectric detector, the evaluation circuit has elements for the evaluation of the voltage signal of the pyroelectric detector, the filter change frequency f is set at a value in the range of the declining branch of the frequency response of the voltage signal, and the pyroelectric detector is selected to be such that the declining branch of the voltage signal has a decline of −20 dB per decade.

15 Claims, 6 Drawing Sheets

OPTICAL GAS ANALYZER

FIELD OF THE INVENTION

The present invention pertains in general to an optical gas analyzer for measuring the percentage of components in a gas sample by means of IR absorption. the analyzer includes a radiation source, a measuring chamber containing the gas sample, a photoelectric receiver detecting the IR radiation from the measuring chamber, an evaluating circuit arranged downstream of the photoelectric receiver and a plurality of filters which can be brought into the beam path one after another at a predetermined filter change frequency f. Measured signals belonging to the filters are received by the photoelectric detector due to the radiation extinction or absorption in the measuring chamber.

BACKGROUND OF THE INVENTION

A gas analyzer for measuring three components of a gas mixture in a gas sample has become known from EP 87 077 A2. A measuring path containing the gas sample is located in the beam path between a radiation source emitting the IR irradiation and a photoelectric receiver converting the radiation into a measured signal. A filter wheel with various filters is arranged in front of the receiver. The filters are permeable in narrow wavelength ranges and are brought cyclically alternatingly into the beam path. The measurement principle of the prior-art device is based on the determination of the extinctions or absorptions in different absorption wavelength ranges of the gas components. Each of the filters sends a wavelength-specific measured signal. To determine the concentrations of the individual components in the gas sample, the numerical values of the individual measured signals are introduced into a set of linear equations, and the concentrations are determined by solving the set of equations. The measuring method of the prior-art gas analyzer is limited by the fact that a set of linear equations must be solved, which requires calculation time. Even though the total number of components to be determined is low in the case of certain applications, e.g., gas analysis in anesthesia, the number of possible components is considerably higher. For example, it is normally also necessary to determine an anesthetic consisting of five possible individual anesthetics besides laughing gas and carbon dioxide. Even though it would be possible to provide a separate filter on the filter wheel for each of the anesthetics, this makes the evaluation difficult because of the large number of filters, especially because reference filters are also needed, besides the measuring filters proper. The problem is made more difficult by the fact that anesthetics may also occur as gas mixtures in the gas sample, e.g., when the anesthetic is changed between two anesthesia.

A gas analyzer for measuring gaseous anesthetics, in which the measuring beam is split into individual beams after passing through the measuring path and is deflected onto individual detectors, has been known from EP 307 625 B1. Filters, whose wavelengths are adapted to the components to be measured, are located in front of the detectors. The number of detectors corresponds to the number of the gases to be detected. The drawback of the prior-art gas analyzer is that the concentration of an anesthetic component present in the gas sample can be determined by means of the measuring system only if the type of the substance, e.g., halothane, isoflurane, or enflurane, is known. The indication of the display unit will be incorrect if the gas analyzer is not set correspondingly to the new anesthetic after a change from one anesthetic to another.

An infrared gas analyzer for measuring carbon dioxide, in which a pyroelectric detector is used to evaluate the measuring radiation, has been known from EP 332 180 A2. This gas analyzer is suitable only for the detection of one component, and the manner in which the measured signal of the pyroelectric detector is processed does not appear from this document.

Connections of pyroelectric detectors which evaluate either the current signal or the voltage signal have been known in the case of the connection for the voltage signal, the frequency response is approximately band pass-shaped, i.e., it first rises, then forms a plateau, and then declines, whereas the current signal also has, in contrast, a band pass characteristic, but with a higher upper cut-off frequency. Such connection possibilities of pyroelectric detectors are described in, e.g., the inhouse publication ELTEC Instruments, Inc., introduction to Infrared Pyroelectric Detectors, ELTEC Date #100, pp. 100-1 to 100-6.

The devices known from the state of the art for detecting a plurality of components in a gas sample differ essentially in whether the measurement is performed simultaneously with a plurality of detectors or sequentially with a single detector and a rotating filter wheel. Even though a measuring setup with a plurality of detectors has the drawback that beam splitting to the detectors is to be performed and drift phenomena of the detectors against each other are to be compensated, the evaluation of the individual measured signals is, on the other hand, relatively problem-free, because a lock-in technique can be used. No special requirements need, in general, be imposed on the frequency response of the detectors, because the measured signal of every detector is a relatively narrow-band signal.

A comparatively simple mechanical design is obtained by the use of a single detector with a rotating filter wheel. However, the detector no longer receives a narrow-band single signal, but a sequence of light pulses I(t), which generate a broadband measured signal, due to the high-speed rotation of the filter wheel. The speed of rotation of the filter wheel is determined by the number of measurements to be performed per unit of time and/or the number of filters on the filter wheel. The advantage of the simple mechanical design is contrasted in the case of a multi-gas measuring device by the problem that the level or the intensity of the individual light pulses should be measured as accurately as possible, without the signals mutually influencing each other.

SUMMARY AND OBJECTS OF THE INVENTION

The basic object of the present invention is to improve a gas analyzer of the above-described type such that different components in a gas sample can be detected in a simple manner and with a good selectivity.

This object is accomplished by a first filter generating a first measured signal S1 and a second filter generating a second measured signal S2. The filters being chosen for measuring anesthetics components, especially sevoflurane, desflurane, halothane, enflurane, and isoflurane. The wavelengths of the filters are in an absorption band between about 7 μm and 18 μm, which is sensitive to anesthetics. The receiver is a pyroelectric detector, and the evaluating circuit has means for evaluating the voltage signal of the pyroelectric detector. The filter change frequency f is set to a value in the range of the declining branch of the frequency response of the voltage signal.

The advantage of the present invention is essentially that irregularities in the characteristic, which influence the measured signal and consequently the selectivity of the detection of the components, are of secondary importance due to the pyroelectric detector being connected for the evaluation of a voltage signal and to the working point, i.e., the filter change frequency, being set on the declining branch of the frequency response of the voltage signal. Even though the current signal of the pyroelectric detector is theoretically nearly independent from the filter change frequency, frequency-dependent variations in amplitude, which make the evaluation difficult, can be observed in the horizontal branch. In contrast, even though the declining branch of the frequency response of the voltage signal shows a frequency-dependent decline in frequency, it is highly uniform and can be approximated, in a good approximation, by a straight line for a large range of the branch in a double-logarithmic plot. A pyroelectric detector having a characteristic with a decline of −20 dB per decade is selected according to the present invention. The utilization of precisely this branch of the characteristic in the frequency response of the voltage signal is especially advantageous for the measurement of a plurality of gas components, because the declining branch of the characteristic can be used to integrate the measured signal, as a result of which the pyroelectric detector, which is slow per se, becomes suitable for applications with time multiplexes of measured signals. The device according to the present invention has made it possible for the first time ever to use pyroelectric detectors for the high-speed, broad-band filter wheel process. The low-pass behavior with a decline of −20 dB per decade is displayed only by special types of pyroelectric detectors. These types have no or only a very thin additional light-absorbing coating (black coating) on the pyroelectric crystal proper. Standard types are provided with a light-absorbing coating in order to increase the sensitivity of the detector. However, these coatings have a thermal time constant of their own, as a result of which the transmission behavior of the entire detector is changed unfavorably precisely at higher frequencies.

Advantageous embodiments of the present invention are described in the subclaims.

A process for identifying a component in a gas sample from a group of N possible components with an infrared gas analyzer, wherein the gas analyzer has at least two and preferably three filters analyzing the component, is characterized by the steps a. generating calibration curves by introducing gas samples containing known percentages of one of the components one after another into a measuring path, recording measured signals with each filter, and relating them to the percentages as characteristic values, b. performing step a. for each of the components, c. determining the component to be identified in the gas sample by recording at least one measured signal with the component to be identified with each of the filters, and determining the corresponding characteristic values of the N components for each measured signal from the calibration curves, and d. selecting the component at which characteristic values located within a predetermined tolerance range with each of the filters as the component to be identified.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6b is an example of a signal evaluation for the light pulses according to FIG. 6a.

DETAILED DESCRIPTION OF THE PREFERRED EMBODIMENT

Figure 1:
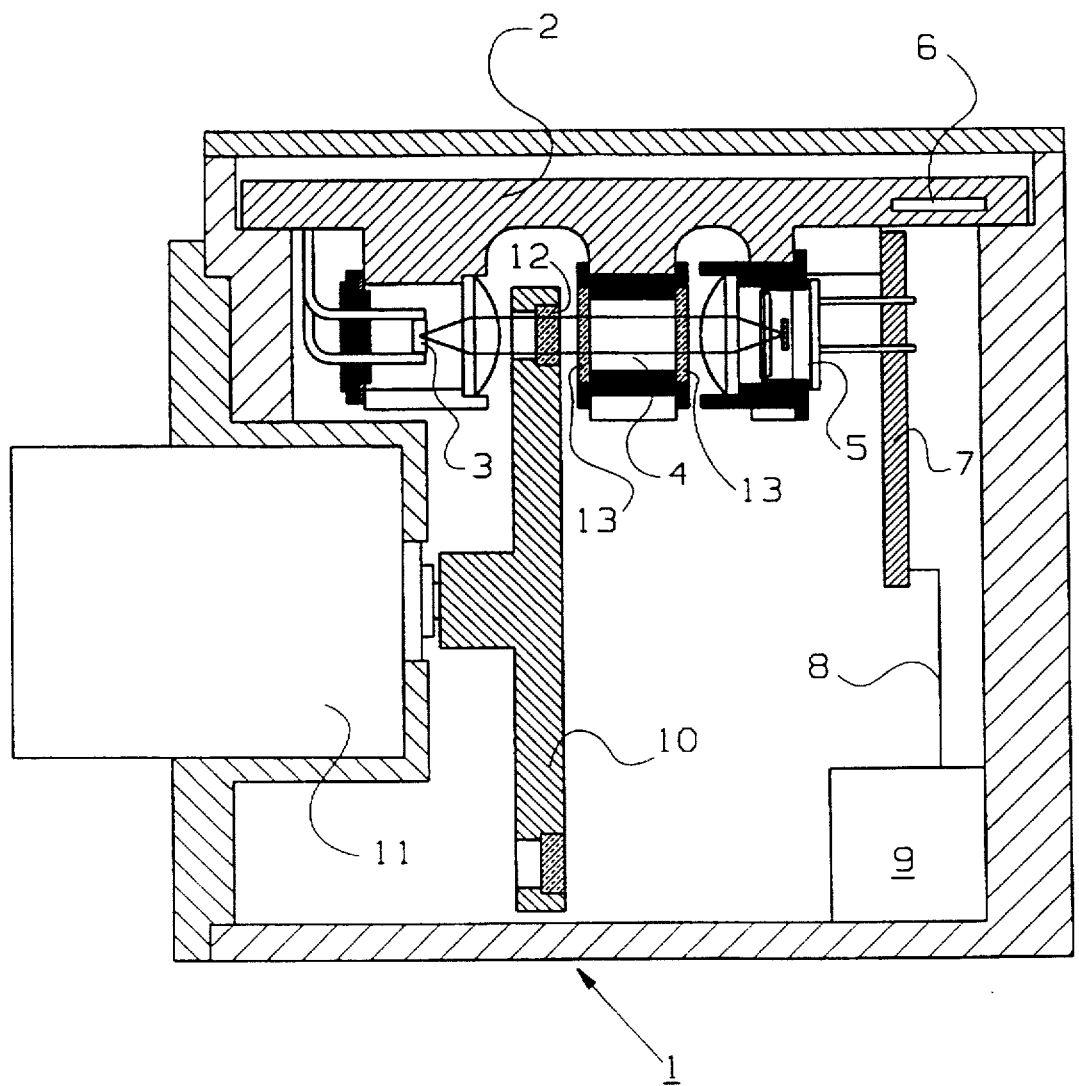
FIG. 1 is a schematic view of a longitudinal section of a gas analyzer.

FIG. 1 schematically shows the longitudinal section of a gas analyzer 1. An IR radiation source 3, a cuvette 4 acting as a measuring path or chamber, and a pyroelectric detector 5 acting as a photoelectric receiver are arranged on a heated support plate 2 in a housing of the gas analyzer 1. The support plate 2 is heated to a temperature of about 55° by means of a heating cartridge 6 located at the support plate 2. The detector 5 is connected to an evaluation circuit 7 and is connected to an electronic evaluation unit 9 via a measured signal line 8. A plurality of filters are introduced one after another by a wheel means into the beam path between the radiation source 3 and the measuring chamber 4 by means of a filter wheel 10 driven by a motor 11. A first filter 12 of these filters is momentarily located in the beam path in FIG. 1. The filter change frequency is about 400 Hz. A first measured signal S1 belonging to the first filter 12 is transmitted to the electronic evaluation unit 9 via the measured signal line 8. The cuvette 4 has windows 13 transparent to IR radiation in the beam path and a gas inlet, not shown in the figure, and a gas outlet for the gas sample to be analyzed.

Figure 2:
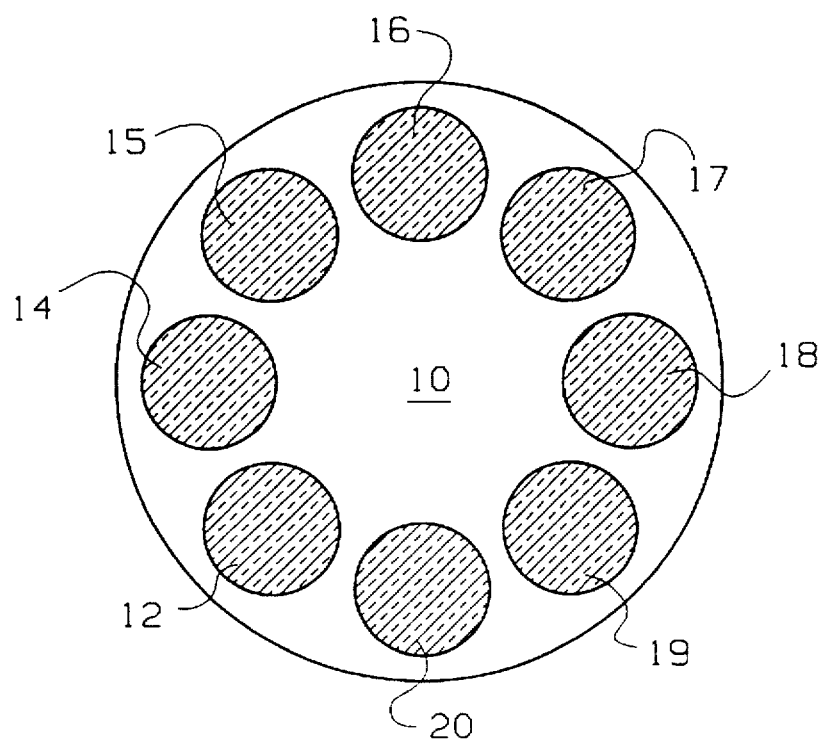
FIG. 2 is a top view of a filter wheel.

FIG. 2 shows a top view of the filter wheel 10. A second filter 14 with the corresponding second measured signal S2, a third filter 15 with the corresponding third measured signal S3, a first reference filter 16 with the corresponding first reference signal, a fourth filter 17 with the corresponding fourth measured signal, a fifth filter 18 with the corresponding fifth measured signal, a second reference filter 19 with the corresponding second reference signal, and a dark filter 20 are present, in addition to the first filter 12 with the corresponding measured signal S1. The first filter 12, with a wavelength of 8.21 µm, the second filter 14, with a wavelength of 8.4 µm, and the third filter 15 with a wavelength of 8.61 µm, are used to measure anesthetics in the gas sample, e.g., halothane, enflurane, or isoflurane. Laughing gas ($N_2O$) is measured with the fourth filter 17, having a wavelength of 3.9 µm, and carbon dioxide present in the gas sample is measured with the fifth filter 18, which has a wavelength of 4.26 µm.

Figure 3A:
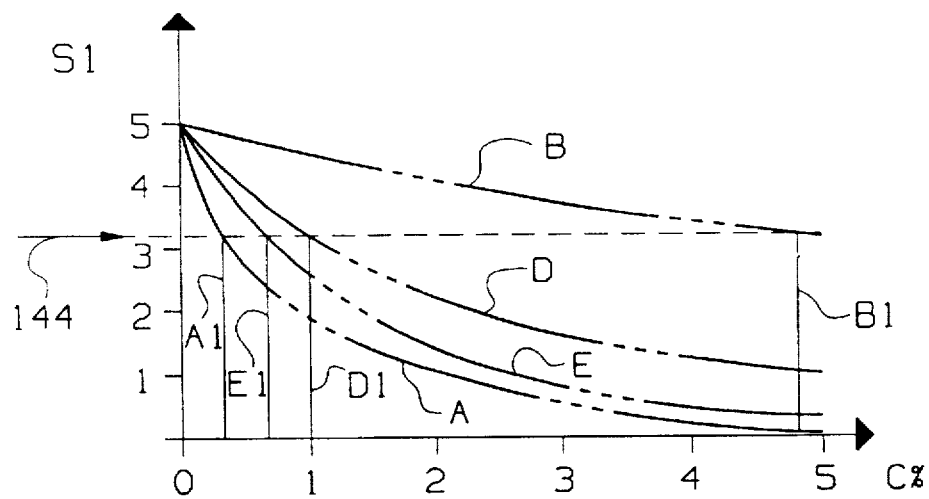
FIG. 3a is calibration curves for anesthetics A, B, D, and E for a first filter.
Figure 3B:
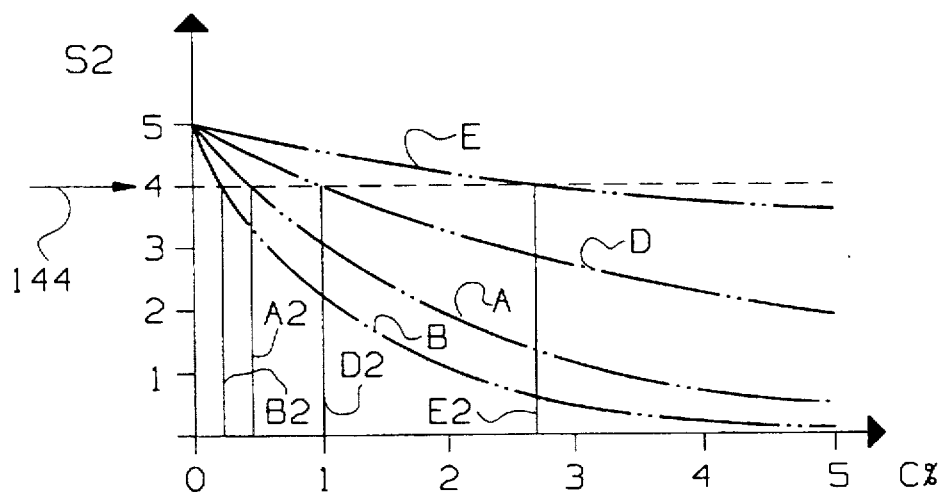
FIG. 3b is calibration curves according to FIG. 3a for a second filter.
Figure 3C:
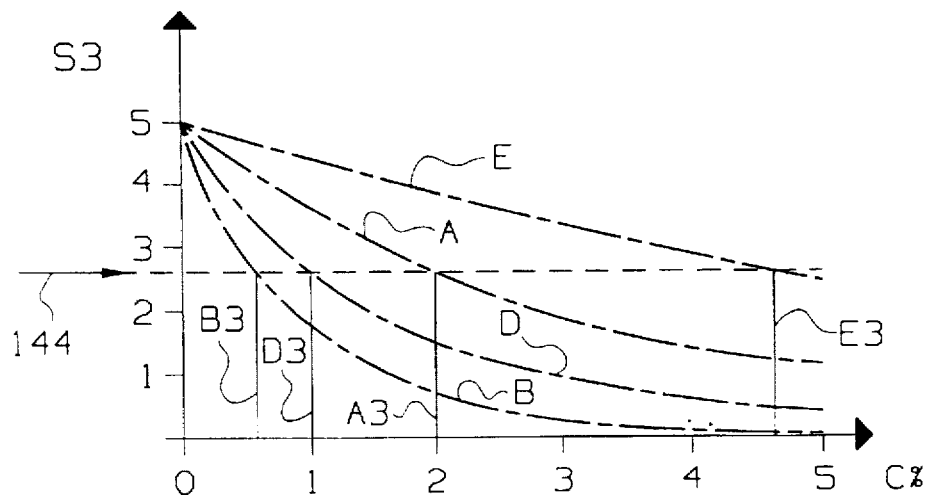
FIG. 3c is calibration curves according to FIG. 3a for a third filter.

The measurement of the anesthetic concentration in the gas sample will be explained below. The following five anesthetics are currently used in inhalation anesthesia: Halothane, enflurane, isoflurane, sevoflurane, and desflurane. It would be possible to provide a separate filter on the filter wheel 10 for each of the anesthetics in order to measure the concentration in the gas sample. In the case of a gas analyzer according to the state of the art, it would thus be necessary to calculate the anesthetic to be determined from a set of equations with five unknowns. In contrast, the anesthetic being sought is determined with the gas analyzer according to the present invention by the comparison of concentration values calculated from the measured signals S1, S2, and S3. Calibration curves A, B, D, and E are recorded for this purpose for the filters 12, 14, 15 at a known anesthetic concentration C. Thus, calibration curve A belongs to halothane, B to enflurane, D to isoflurane, and E to sevoflurane. The calibration curve for desflurane is not shown for the sake of greater clarity. The calibration curves A, B, D, and E are illustrated in FIGS. 3a, 3b, and 3c. FIG. 3a shows the calibration curves A, B, D, E belonging to the first filter 12. The anesthetic concentration C in percent is shown on the abscissa, and the first measured signal S1 is shown on the ordinate. The calibration curves for the second filter 14 are correspondingly shown in FIG. 3b, and the calibration curves for the third filter 15 are shown in FIG. 3c.

The measurement procedure for determining the concentration is as follows:

A first measured signal S1 of, e.g., 3.2 (FIG. 3a) is measured with the first filter 12 in a gas sample containing an unknown percentage of anesthetic. A second measured signal S2 of, e.g., 4.0 (FIG. 3b) is obtained with the second filter 14. The third filter 15 yields a third measured signal S3 of 2.6 (FIG. 3c). The numerical values for S1, S2, and S3 are marked by arrows 144 on the ordinates in FIGS. 3a through 3c. Corresponding concentration values A1, B1, D1, and E1 are obtained from the first measured signal S1=3.2 by means of the calibration curves A, B, D, and E; the concentration values A2, B2, D2, and E2 are obtained from the second measured signal S2=4.0; and the concentration values A3, B3, D3, and E3 are obtained from the third measured signal S3=2.6. The anesthetic being sought and the corresponding percentage content of anesthetic in the gas sample are obtained from the condition that equal concentration values occur for each of the filters 12, 14, 15 for one of the calibration curves A, B, D, and E. In this case, D1=D2=D3= 1%, i.e., isoflurane—curve D—is the anesthetic sought, and the percentage of isoflurane in the gas sample is 1%. A corresponding identification of an anesthetic can also be performed with a larger number of possible anesthetics.

However when only two filters are used, a mixture of two anesthetics cannot be prevented from mimicking the presence of a third anesthetic. This can be prevented by the use of three filters.

Figure 4:
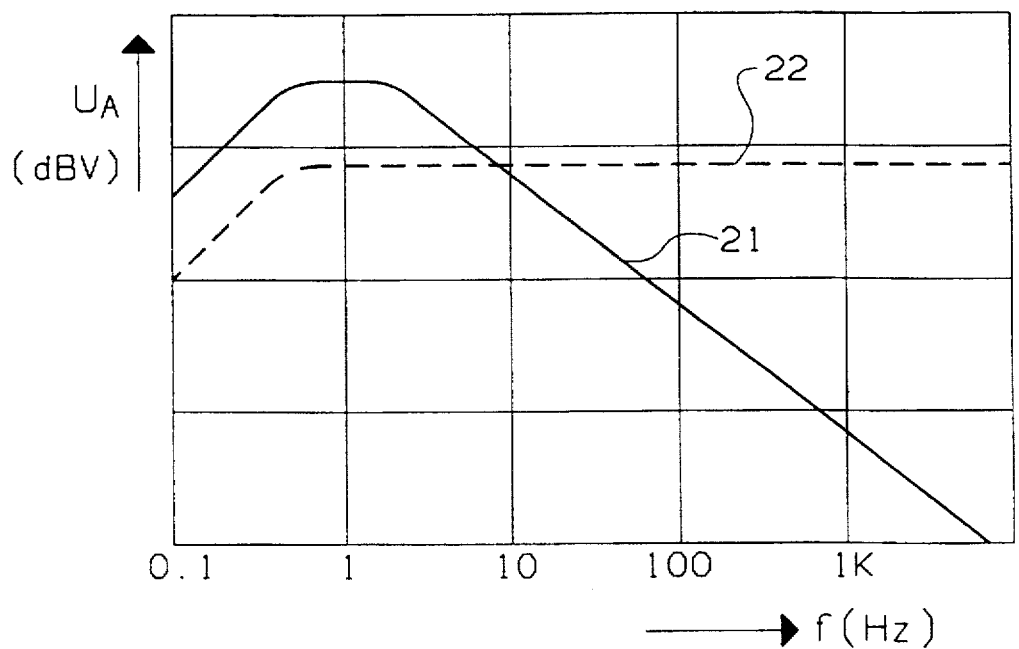
FIG. 4 is characteristics of a pyroelectric detector.

FIG. 4 illustrates the shape of the characteristic of the pyroelectric detector 5. The filter change frequency f is shown on a logarithmic scale on the abscissa, and the output voltage $U_A$ of the evaluating circuit 7 is shown on the ordinate. Curve 21 shows the frequency response of the pyroelectric detector 5 for an evaluating circuit 7 processing the voltage signal $U_r$, and curve 22 shows the corresponding shape of the current signal. The curves 21, 22 are shown in an idealized form in FIG. 4. For example, frequency-dependent variations in amplitude, which are not shown in FIG. 4, occur in practice ill curve 22. While curve 22 possesses essentially high-pass properties, curve 21 has essentially band pass properties. Curve 21 first displays an increase in the signal, and the output voltage $U_A$ decreases uniformly by about 20 dB per frequency decade after passing through a plateau.

Figure 5:
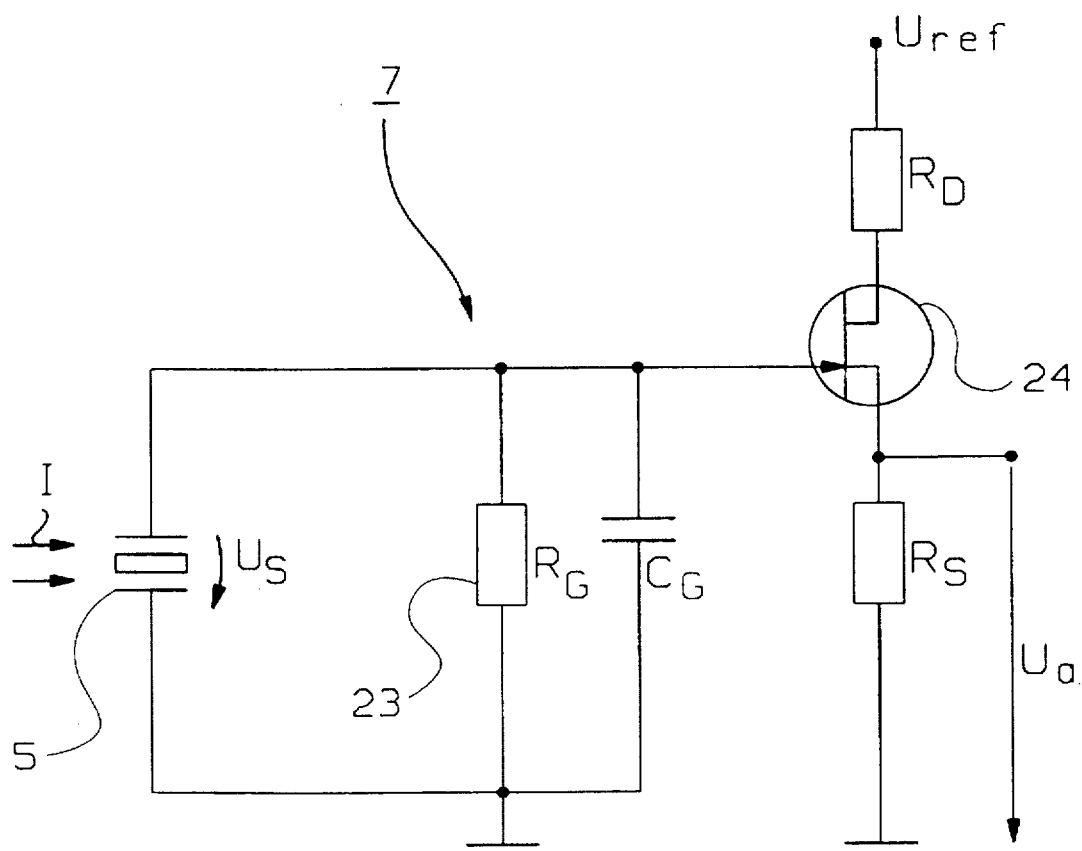
FIG. 5 is an evaluation circuit for the voltage signal of the pyroelectric detector.

FIG. 5 shows the pyroelectric detector 5 with the part of the evaluating circuit 7 for processing its voltage signal $U_r$, which part is arranged immediately downstream of it. The pyroelectric detector 5 is connected to a field-effect transistor (FET) 24 via a high-ohmic gate resistor 23.

Figure 6A:
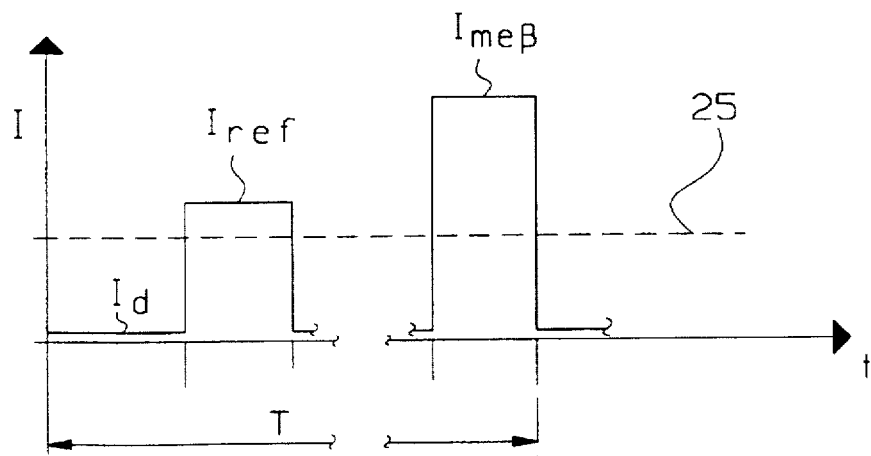
FIG. 6a is a sequence of light pulses I(t)

FIG. 6a shows as an example the sequence of individual light pulses $L_{ref}$ and $I_{mes}$ relative to a dark signal $I_d$. For example, the signal $I_{ref}$ or $I_{mes}$ is obtained when one of the reference filters 16, 19 or one of the filters 12, 14, 15, 17, 18 is located in the beam path. The time interval T corresponds to one complete revolution of the filter wheel 10. The dark signal $I_d$ becomes established at the time of the change from one filter to an adjacent filter.

The basic principle of the evaluation of such a sequence of light pulses is to determine the mean value, i.e., the plateau of the light pulse $I_{ref}$ and $I_{mes}$ relative to $I_d$. This value is proportional to the light intensity of the corresponding channel. Since the light pulses have a very high harmonic content because of the rectangular shape of the signal, a detector that transmits all frequency components with equal sensitivity must be available for the evaluation. If the current signal (curve 22, FIG. 4) of the pyroelectric detector 5 were used, the frequency-dependent amplitude variations occurring in the amplitude characteristic, which are not shown in FIG. 4 for the sake of clarity, would have to be eliminated with expensive compensation circuits.

These amplitude variations do not occur in the declining branch of the voltage signal (curve 21, FIG. 4). If the pyroelectric detector 5 is selected to be such that the declining branch of the voltage signal has a decline of −20 dB per decade in a double-logarithmic plot, the integral of the plateau of the light pulse can be directly evaluated, which is equivalent to a peak value determination. Expensive compensation circuits, which would have been necessary in the case of the evaluation of the current signal (curve 22, FIG. 4), are avoided by shifting the evaluation to the declining branch of the voltage signal.

Figure 6B:
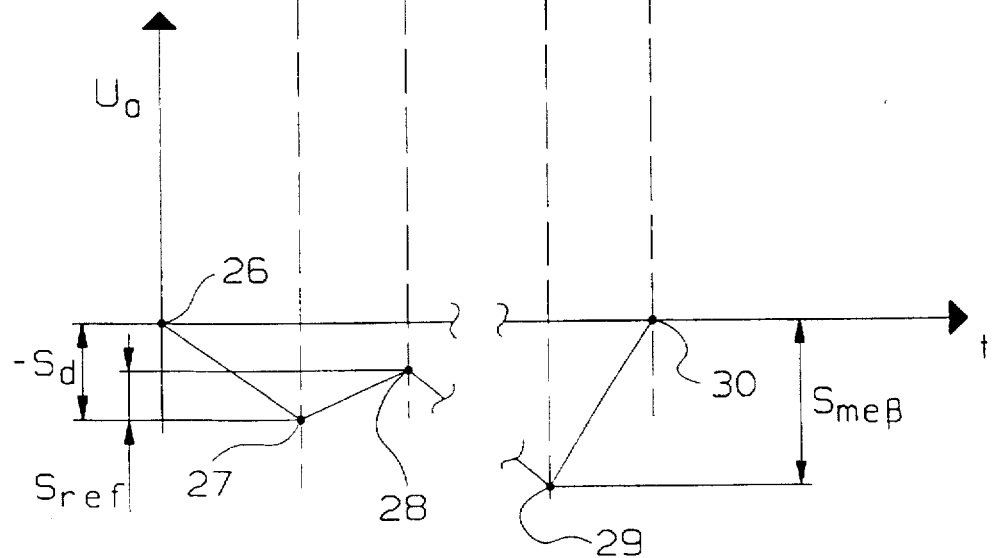

FIG. 6b illustrates the integration of the light pulses $I_d$, $I_{ref}$, and $I_{mes}$ with the pyroelectric detector 5 and with the evaluation circuit 7 according to FIG. 5. The constant light component of the signal I(t) (FIG. 6a) is left out of consideration in the integration because of the high-pass behavior of curve 21 in FIG. 4 in the range of up to about 0.8 Hz. The constant light component is schematically represented as a horizontal line 25 in FIG. 6a. Sections with different slopes and corresponding integration initial and end values 26, 27, 28, 29, 30 are obtained by integrating the light pulses $I_d$, $I_{ref}$ and $I_{mes}$. A measured value $S_{ref}$ that is proportional to $I_{ref}$ is obtained by forming the difference of the end values 28, 27, and a measured value $S_{mes}$, which is proportional to $I_{mes}$, is obtained by forming the difference of end values 29,30. $S_{mes}$ represents the measured signals S1, S2, S3. A measured value $S_d$, which is proportional to $I_d$, is obtained by forming the difference from the integration values 27 and 26 belonging to the integration of $I_d$.

The measured values $S_{mes}$, $S_{ref}$ and $S_d$ are proportional to the chopped light component of the light signals $I_{mes}$, $I_{ref}$ and $I_d$.

The plateau values of the light signals $I_{mes}$ and $I_{ref}$ relative to the dark signal $I_d$ are now proportional to the differences $S_{mes}-S_d$ and $S_{ref}-S_d$. $I_{ref}-I_d$ is proportional to $S_{ref}-S_d$, and $I_{mes}-I_d$ is proportional to $S_{mes}-S_d$. The output voltage $U_a$ again assumes the "zero" value after the period T due to the uncoupling of the d.c. voltage component, the horizontal line 25.

While specific embodiments of the invention have been shown and described in detail to illustrate the application of the principles of the invention, it will be understood that the invention may be embodied otherwise without departing from such principles.

What is claimed is:

1. An optical gas analyzer comprising:
   a radiation source;
   a measuring chamber capable of containing a gas sample, said measuring chamber receiving radiation from said radiation source;
   a plurality of filters positionable in a beam path from said radiation source to said measuring chamber;
   a photoelectric receiver receiving radiation from said radiation source through said measuring chamber, said photoelectric receiver generating a voltage signal in proportion to a received amount of said radiation, said voltage signal of said photoelectric receiver having a frequency response with a declining branch;
   filter wheel means for moving said plurality of filters into and out of said beam path at a filter change frequency f, said filter change frequency f being in said declining branch of said frequency response.

2. An analyzer in accordance with claim 1, wherein:
   said photoelectric receiver is a pyroelectric detector and said voltage signal of said pyroelectric detector is in proportion to IR radiation;
   a first of said plurality of filters causes a first measured signal due to radiation extinction in said measuring chamber and a second of said plurality of filters causes a second measured signal for measuring anesthetics due to radiation extinction in said measuring chamber, said filters having wavelengths between 7 and 18 microns;
   an evaluating circuit means connected to said photoelectric receiver and for evaluating said voltage signal.

3. An analyzer in accordance with claim 2, wherein:
   said measured signals of said first and second filters are for measuring one of sevoflurane, desflurane, halothane, enflurane and isoflurane.

4. An analyzer in accordance with claim 2, wherein:
   a third of said plurality of filters causes a third measured signal due to radiation extinction in said measuring chamber.

5. An analyzer in accordance with claim 2, wherein:
   said evaluation circuit means includes a field-effect transistor (FET) positioned downstream of said pyroelectric detector and acts as an impedance converter with a high-ohmic gate resistor acting as a current-voltage converter.

6. An analyzer in accordance with claim 2, wherein:
   a difference between said wavelengths of said plurality of filters is not less than 0.10 μm, and that a difference between a highest and lowest wavelength of said plurality of filters is less than 9 μm.

7. An analyzer in accordance with claim 2, wherein:
   said first of said plurality of filters has a wavelength of substantially 8.21 μm, said second of said plurality of filters has a wavelength of substantially 8.4 μm, and a third of said plurality of filters has a wavelength of substantially 8.61 μm, said plurality of filters includes a reference filter for forming a reference measured signal for said measured signals.

8. An analyzer in accordance with claim 7, wherein:
   a wavelength of said reference filter is substantially 10.5 μm.

9. An analyzer in accordance with claim 7, wherein:
   said plurality of filters includes another reference filter with a wavelength of substantially 3.69 μm for forming another reference signal for measuring one of $N_2O$ and carbon dioxide.

10. An analyzer in accordance with claim 2, wherein:
    a third of said plurality of filters has a wavelength of substantially 3.9 μm and is provided for measuring $N_2O$.

11. An analyzer in accordance with claim 10, wherein:
    a fourth of said plurality of filters has a wavelength of substantially 4.26 μm and is provided for measuring carbon dioxide.

12. An analyzer in accordance with claim 2, wherein:
    a difference between said wavelengths of said plurality of filters is not less than 0.10 μm, and that a difference between a highest and lowest wavelength of said plurality of filters is less than 9 μm for measuring one of sevoflurane, desflurane, halothane, enflurane, or isoflurane.

13. An analyzer in accordance with claim 1, wherein:
    a length of said measuring chamber is 5 to 15 mm.

14. An analyzer in accordance with claim 1, wherein:
    said declining branch of the said voltage signal has a decline of −20 dB per decade.

15. A process for identification of a component in a gas sample from a group of N possible components, the process comprising the steps of:
    providing an infrared gas analyzer with two filters and a measuring chamber;
    generating a calibration curve for each of the N possible components by introducing respective gas samples containing a known percentage of a respective one of the N possible components into the said measuring path, recording measured signals with each of said filters and relating said measured signals to percentages as characteristic values;
    recording at least one measured signal from the gas sample with each of said filters;
    determining corresponding characteristic values of the N components for each said measured signal from said calibration curves;
    selecting one of the N possible components at which the determined characteristic values for each filter are located within a predetermined tolerance range as the component to be identified.

* * * * *